(12) United States Patent
Barnett et al.

(10) Patent No.: US 10,682,320 B2
(45) Date of Patent: Jun. 16, 2020

(54) METHOD FOR INHIBITING OSTEOCLAST DEVELOPMENT

(71) Applicants: West Virginia University, Morgantown, WV (US); University of Pittsburgh-Of the Commonwealth System of Higher Education, Pittsburgh, PA (US); Temple University-Of the Commonwealth System of Higher Education, Philadelphia, PA (US)

(72) Inventors: John B. Barnett, Morgantown, WV (US); Harry C. Blair, Pittsburgh, PA (US); Jonathan Soboloff, Cheltenham, PA (US)

(73) Assignees: West Virginia University, Morgantown, WV (US); Temple University-Of the Commonwealth System of Higher Education, Philadelphia, PA (US); University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 658 days.

(21) Appl. No.: 13/864,438

(22) Filed: Apr. 17, 2013

(65) Prior Publication Data
US 2013/0303621 A1 Nov. 14, 2013

Related U.S. Application Data

(60) Provisional application No. 61/635,525, filed on Apr. 19, 2012.

(51) Int. Cl.
*A61K 31/167* (2006.01)
(52) U.S. Cl.
CPC .................... *A61K 31/167* (2013.01)
(58) Field of Classification Search
None
See application file for complete search history.

(56) References Cited

FOREIGN PATENT DOCUMENTS

GB 1063528 A * 3/1967 .......... C07C 233/02

OTHER PUBLICATIONS

Zhou et al., The Role of Calcium Release Activated Calcium Channels in Osteoclast Differentiation, J. Cell. Physiol. 226: 1082-1089, 2011. β 2010 Wiley-Liss, Inc, Published online in Wiley Online Library (wileyonlinelibrary.com) on Sep. 13, 2010.*
Patani et al., Bioisosterism: A Rational Approach to Drug Design, Chem.Rev. 1996, 96, 3147-3176.*
Homolog, Illustrated Glossary of Organic Chemistry, www.chem.ucla.edu, Sep. 8, 2009, printed Aug. 10, 2017 from http://www.chem.ucla.edu/~harding/IGOC/H/homolog.html, Google date of internet entry of Sep. 8, 2009 included, 2 pages.*
Sharabi et al., Biochemical decomposition of the herbicide N-(3,4-dichlorophenyl)-2-methylpentanamide and related compounds, Appl Microbiol. Sep. 1969;18(3):369-75, Abstract only, 1 page.*

* cited by examiner

*Primary Examiner* — GiGi G Huang
(74) *Attorney, Agent, or Firm* — Buchanan Ingersoll & Rooney PC; Craig G. Cochenour, Esq.

(57) ABSTRACT

This invention provides a composition comprising Formula I, or salt thereof,

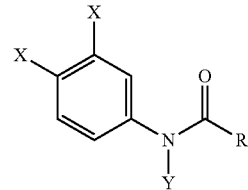

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except that X is not chlorine when Y is hydrogen and R is an ethyl group. A method of preventing bone erosion in a patient and a method of reducing inflammation in a patient using the compositions of Formula I are disclosed.

2 Claims, 10 Drawing Sheets

*N*-(3,4-dichlorophenyl)propionamide

*N*-(3,4-dibromophenyl)propionamide

*N*-(3,4-dichlorophenyl)-*N*-methylpropionamide

*N*-(3,4-dichlorophenyl)isobutyramide

*N*-(3,4-dichlorophenyl)-*N*-methylisobutyramide

METHOD FOR INHIBITING OSTEOCLAST DEVELOPMENT

CROSS-REFERENCE TO RELATED APPLICATION

This utility patent application claims the benefit of priority to U.S. Provisional Patent Application Ser. No. 61/635,525 filed Apr. 19, 2012. The entire contents of U.S. Provisional Patent Application Ser. No. 61/635,525 are incorporated by reference in its entirety into this utility patent application.

STATEMENT REGARDING FEDERALLY SPONSORED RESEARCH

This invention was made with government support under Grant Nos. R01 AG 012951, R01 AR 053566, R01 ES 011311, R01 AR 065407, and R01 AR 053976 awarded by the National Institute of Health. The Government has certain rights in this invention.

BACKGROUND OF THE INVENTION

1. Field of the Invention

The present invention provides a method for inhibiting osteoclast development and a method for preventing bone erosion by delivering an effective amount of a haloanilide to an osteoclast for inhibiting the osteoclast development and preventing bone erosion. Preferably, the haloanilide is N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide, or N-(3,4-dichlorophenyl)-N-methylisobutyramide.

2. Background Art

The composition N-(3,4-dichlorophenyl)propanamide ("DCPA") is commercially available under the tradename "Propanil" for use as a herbicide. Its primary use in to control grassy weeds in rice fields because rice, as well as wheat, has naturally higher levels of acylamidase. Acylamidase enzymatically breaks DCPA into dichloroaniline (DCA) and water, thus inactivating the herbicide qualities of the DCPA. DCA is not toxic to plants, and the rice is unharmed but grassy weeds, which have low natural levels of acylamidase, are killed by the herbicide DCPA. Generally, the herbicide DCPA is applied numerous times during a growing season, often by spray plane because the rice is grown under very wet conditions.

The toxicity of DCPA has been investigated. It is actually of low systemic toxicity. Mice can tolerate doses in excess of 100 mg/kg and only doses >150 mg/kg produce frank immunotoxicity. The metabolism of DCPA by acylamidase produces DCA as mentioned above. DCA is then metabolized to N—OH-DCA and 6-OH-DCA. Both N—OH-DCA and 6-OH-DCA contribute to the systemic toxicity associated with in vivo administration of DCPA.

It is known that DCPA is anti-inflammatory. DCPA is capable of reducing the secretion of pro-inflammatory cytokines from macrophages both in vivo and ex vivo. The mechanism of the anti-inflammatory effect of DCPA was first determined in 1997. This mechanism is that DCPA is capable of inhibiting intracellular calcium release in macrophages.

SUMMARY OF THE INVENTION

This invention provides a composition comprising a haloanilide, or salt thereof, that is a selective inhibitor of a $Ca^{2+}$ release activated $Ca^{2+}$ (CRAC) channel, wherein the haloanilide composition is not N-(3,4-dichlorophenyl)propanamide.

In a preferable embodiment of this invention, compositions of this invention are provided comprising Formula I, or a salt thereof,

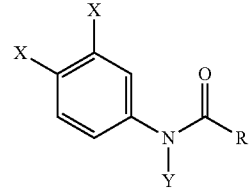

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except that wherein X is not chlorine when Y is hydrogen and R is an ethyl group. More preferably, the compositions of this invention include wherein the alkyl group has from three to five carbon atoms and the carbon atoms are in either a straight chain or a branch chain arrangement. The compositions of Formula I preferably include wherein R is an ethyl group or wherein R is an isopropyl group. Most preferably, the compositions of this invention are selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

Another embodiment of this invention provides a method of inhibiting osteoclast development comprising administering an effective amount of a haloanilide composition of this invention or a salt thereof, to an osteoclast cell for inhibiting osteoclast development, wherein the haloanilide composition is not N-(3,4-dichlorophenyl)propanamide ("DCPA"). A preferred embodiment of this invention provides wherein the haloanilide composition of this invention is a composition of Formula I, or salt thereof, comprising

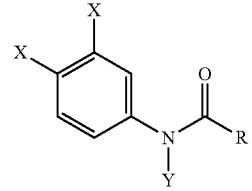

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except wherein X is not chlorine when Y is hydrogen and R is an ethyl group. More preferably, this method as described herein, includes wherein the alkyl group has from three to five carbon atoms and the carbon atoms are in either a straight chain or a branch chain arrangement. This method of this invention, as described herein, preferably includes wherein R is an ethyl group, or wherein R is an isopropyl group. Most preferably, this method includes wherein Formula I is a composition selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

Another embodiment of the present invention provides a method for preventing bone erosion, especially in a patient diagnosed with arthritis, comprising administering to a patient an effective amount of a haloanilide composition of this invention, or a salt thereof, for preventing bone erosion, especially due to arthritis, in a patient, wherein the haloanilide composition is not N-(3,4-dichlorophenyl)propanamide. Preferably, this method includes wherein the haloanilide is a composition of Formula I, or salt thereof, comprising

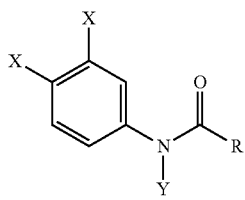

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, wherein X is not chlorine then Y is hydrogen and R is an ethyl group, except wherein X is not chlorine when Y is hydrogen and R is an ethyl group. More preferably, this method, as described herein, includes wherein the alkyl group has from three to five carbon atoms and the carbon atoms are in either a straight chain or a branch chain arrangement. This method of this invention preferably includes wherein the R is an ethyl group or an isopropyl group. Most preferably, this method, as described herein, includes wherein Formula I is a composition selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

Another embodiment of this invention provides a method of inhibiting a Ca$^{2+}$ release activated Ca$^{2+}$ (CRAC) channel either in vivo or in vitro comprising subjecting a cell derived from a blood monocyte to an effective amount of a haloanilide composition of this invention, or salt thereof, for inhibiting a Ca$^{2+}$ release activated Ca$^{2+}$ (CRAC) channel of the cell, wherein the haloanilide composition is not N-(3,4-dichlorophenyl)propanamide. In a preferred embodiment of this method, as described herein, the haloanilide is a composition of Formula I, or salt thereof, comprising

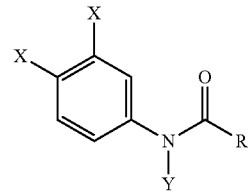

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except wherein X is not chlorine when Y is hydrogen and R is an ethyl group. More preferably, the method includes wherein the alkyl group has from three to five carbon atoms and the carbon atoms are in either a straight chain or a branch chain arrangement. This method, as described herein, preferably includes wherein R is an ethyl group or an isopropyl group. Most preferably, this method, as described herein, includes wherein the haloanilide is composition selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

In another embodiment of this invention, a method of reducing inflammation in a patient is provided comprising administering to a patient an effective amount of a haloanilide composition or salt thereof, for reducing inflammation in a patient, wherein the haloanilide composition is not N-(3,4-dichlorophenyl)propanamide. Preferably, this method of reducing inflammation in a patient includes wherein the haloanilide is a composition of Formula I, or salt thereof, comprising

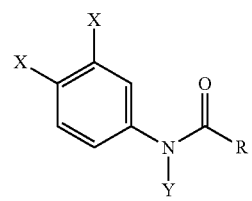

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, wherein X is not chlorine then Y is hydrogen and R is an ethyl group, except wherein X is not chlorine when Y is hydrogen and R is an ethyl group. More preferably, this method of reducing inflammation in a patient includes wherein the alkyl group has from three to five carbon atoms and the carbon atoms are in either a straight chain or a branch chain arrangement. More preferably, this method of reducing inflammation in a patient includes wherein the R is either an ethyl group or an isopropyl group. Most preferably, this method of reducing inflammation comprises administering to a patient an effective amount of the composition of Formula I that is selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3, 4-dichlorophenyl)-2-dimethylpropanamide, N-(3,4-dichlorophenyl)isobutyramide, and N-(3,4-dichlorophenyl)-N-methylisobutyramide, for reducing inflammation in the patient.

BRIEF DESCRIPTION OF THE DRAWINGS

FIGS. 1A-E show store operated calcium entry (SOCe) measured in monocytes maintained in m-CSF. The insets of FIGS. 1A-E depict each individual cell within the boxed regions to reveal $Ca^{2+}$ fluxes during the period prior to the addition of Tg.

FIG. 2A shows transfection of a mixture of four siRNAs to reduce Orai I expression. FIG. 2B shows a Western Blot siRNAs Orai I protein after three days of transfection relative to controls transfected with scrambled siRNA. FIG. 2C shows Orai I mRNA quantified in transfected and control cells relative to GAPDH by use of quantitative real-time PCR as a function of time. After three days, mRNA is reduced but the siRNA is progressively lost. FIG. 2D shows treatment of cell cultures for 7 days with RANKL relative to the same medium without RANKL did not affect Orai I mRNA level relative to GAPDH, which suggest that expression is not down-regulated by osteoclast differentiation. FIG. 2E shows cells with Orai I knocked down produce few nucleated cells. Cells were maintained in osteoclast differentiation medium with RANKL and m-CSF, for seven days after transfection. Multinucleated cells were reduced about 70% by knockdown and very few cells with more than three nuclei were present (black bars) relative to control (gray bars).

DETAILED DESCRIPTION OF THE INVENTION

Figure 1:
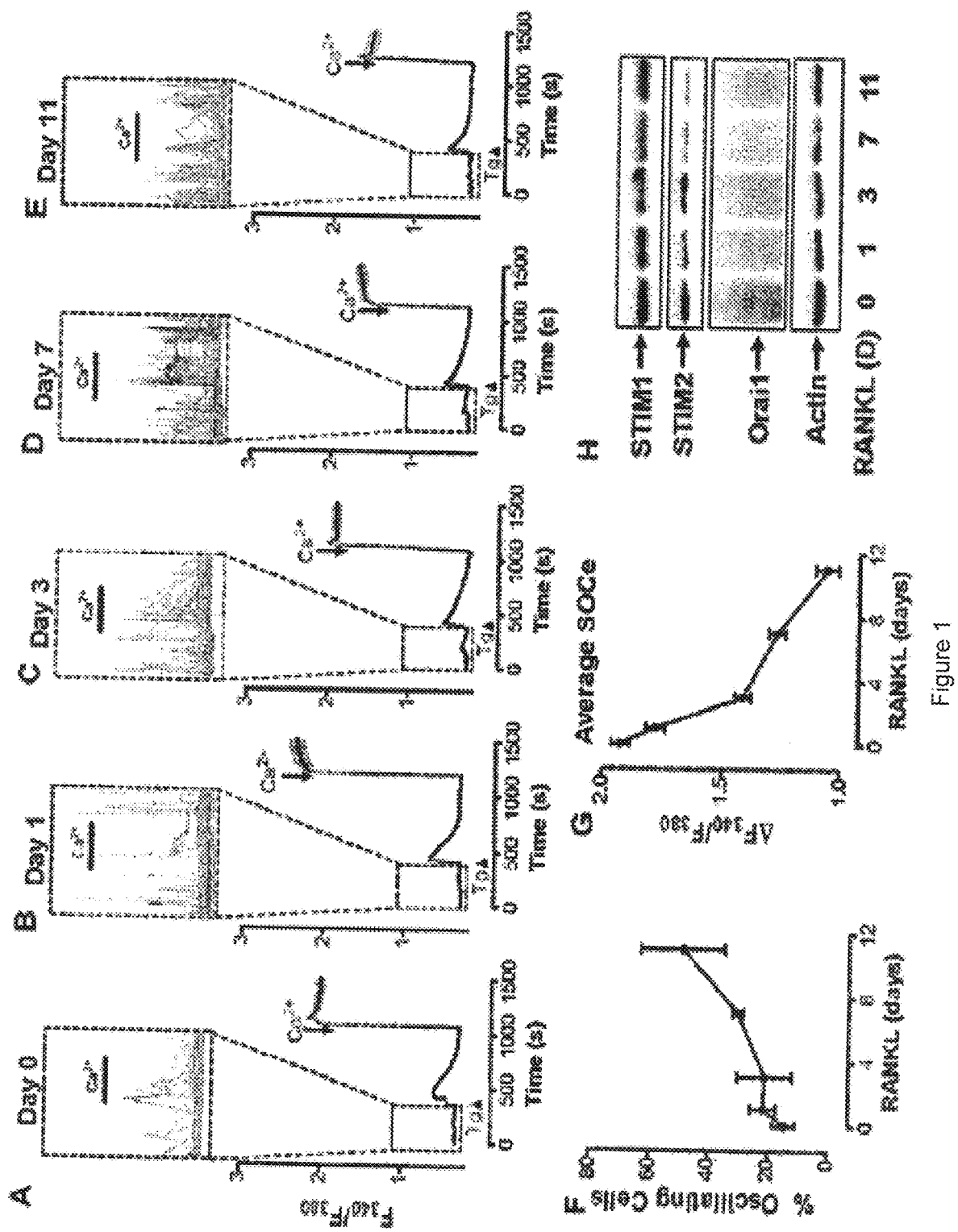
FIGS. 1A-E show modulation of store-operated calcium channels during osteoclast differentiation.
FIG. 1F shows the percentage of cells exhibiting $Ca^{2+}$ fluxes as depicted in FIGS. 1A-E.
FIG. 1G shows the total amount of store-operated $Ca^{2+}$ entry at each time point.
FIG. 1H is a Western Blots for STIM I, STIM2, and Orai I and Actin in isolated monocytes maintained in m-CSF (day zero) and supplemented with RANKL for 1, 3, 7, or 11 days.

The present invention investigated the effect of N-(3,4-dichlorophenyl)propanamide ("DCPA") on calcium influx in a T cell line as well as HEK cells (fibroblast cell line often used for cellular physiology). The calcium ($Ca^{2+}$) release activated calcium ($Ca^{2+}$) ("CRAC") channel is fully characterized in T cells. The present invention shows that DCPA inhibits CRAC channel activity which prevents calcium influx necessary for T cell activation (cytokine production). DCPA inhibits calcium influx in macrophages. Macrophages are tissue bound cells that are derived from blood monocytes under the influence of specific growth factors and cytokines. Other cell types that are also derived from blood monocytes include osteoclasts. Osteoclasts destroy bone and are one of two main cells that maintain the normal homeostasis of bones. Bone is not a static tissue and there is a constant breakdown of bone by osteoclasts balanced with new bone formation by osteoblasts. Patients with arthritis (osteoarthritis and rheumatoid arthritis) have an imbalance of this process and there is an excess of osteoclast activity with leads to joint deformity. Heretofore, there was no treatment available to prevent this excess bone erosion. The present invention shows that haloanilide compositions, and their salts, and preferably haloanilides selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl) isobutyramide, and N-(3,4-dichlorophenyl)-N-methylisobutyramide, inhibits osteoclast production from human blood monocytes in a concentration-dependent manner. The present invention shows that osteoclasts also utilize CRAC channels for activation and that the haloanilide compositions of this invention inhibit CRAC activity in monocytes and that the key activity that required CRAC activity was forming the multinuclear syncytia characteristic of osteoclasts. The present invention shows that the haloanilide compositions of this invention inhibit CRAC activity by preventing the formation of punctae by a substructure of the CRAC channel called STIM1. The present invention shows that haloanilide compositions such as for example but not limited to N-(3,4-dibromophenyl)propanamide, N-(3,4-dichlorophenyl)-N-methylpropanamide, N-(3, 4-dichlorophenyl)-N,2-dimethylpropanamide), N-(3,4-dichlorophenyl)-2-dimethylpropanamide, N-(3,4-dichlorophenyl)isobutyramide, and N-(3,4-dichlorophenyl)-N-methylisobutyramide, inhibit the formation of collagen-induced arthritis (CIA) in mice dramatically. CIA is the most commonly used animal model for arthritis. The haloanilide compositions, and salts thereof, of this invention, inhibit CRAC channel activity and may be administered to patients to prevent bone erosion associated with arthritis. Other known CRAC channel inhibitors are far too toxic to be considered drug candidates.

The metabolism of DCPA by acylamidase produces DCA as mentioned above. DCA is then metabolized to N—OH-DCA and 6-OH-DCA. Both N—OH-DCA and 6-OH-DCA contribute to the systemic toxicity associated with in vivo administration of DCPA. However, the present inventor has found that the effect of DCA, N—OH-DCA and 6-OH-DCA on intracellular calcium influx and their toxicity was not associated with CRAC channel inhibition. Thus, the CRAC channel inhibitory activity of DCPA is not attributable to any of these toxic metabolites. Given that the CRAC channel inhibition associated with DCPA was not due to the more toxic metabolites, the present invention discloses haloanilide compositions of Formula I, and salts thereof that are not metabolized to DCA but that have similar CRAC channel inhibitory qualities of DCPA:

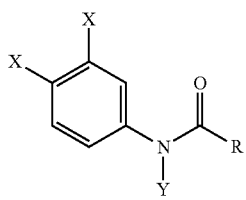

Figure 4:
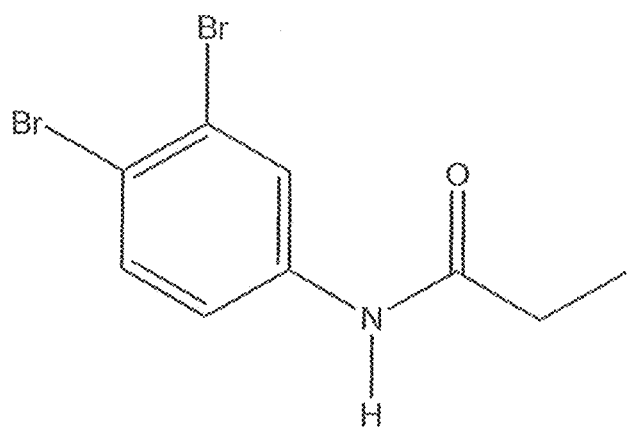
FIG. 4 shows the chemical structures of the more preferred haloanilide compositions of the present invention, namely, N-(3,4-dibromophenyl)propionamide (also known as "DBPA" or "N-(3,4-dibromophenyl)propanamide"), and N-(3,4-dichlorophenyl)-N-methylpropionamide (also known as "N,N-Me,Propyl-CA" or "N-Methyl-DCPA" or "NMP" or "N-(3,4-dichlorophenyl)-N-methylpropanamide").
Figure 4:
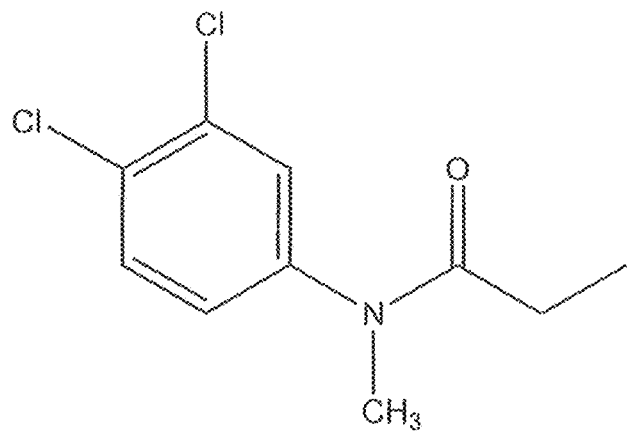
Figure 5:
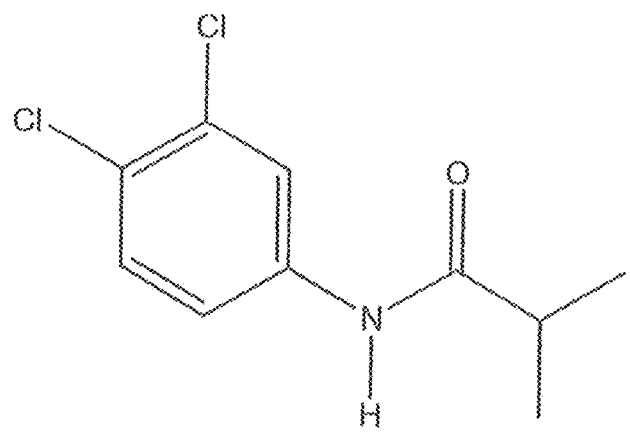
FIG. 5 shows the chemical structures of the more preferred haloanilide compositions of the present invention, namely, N-(3,4-dichlorophenyl)isobutylamide (also known as "N-Isobutyl-CA" or "DNI"), and N-(3,4-dichlorophenyl-N-methylisobutyramide (also known as "N,N-Me,Isobutyl-CA").
Figure 5:
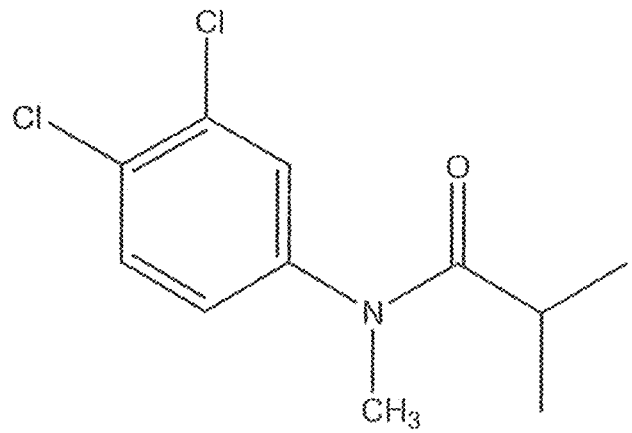

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except wherein X is not chlorine when Y is hydrogen and R is an ethyl group. Synthesis routes for N-(3,4-dibromophenyl)propanamide [also referred to as "DBPA" or "N-(3,4-bibromophenyl) propionamide"], N-(3,4-dichlorophenyl)-N-methylpropanamide [also referred to as "N-Methyl Propanil"; or "N-Methyl-DCPA"; or "NMP"; or "NM Propanil"; or "N-(3,4-dichlorophenyl)-N-methylpropionamide"; or "N,N-Methyl, Propyl-CA" (CA=carboxamide)], 3,4-dichloro-N-methyl-N-isobutyramide [also referred to as "N-(3,4-dichlorophenyl)-N,2-dimethylpropanamide"; or "DNMI"], N-(3,4-dichlorophenyl)-2-dimethylpropanamide, N-(3,4-dichlorophenyl)isobutyramide [also referred to as "DNI" or "N-Isobutyl-CA" (CA=carboxamide)], and N-(3,4-dichlorophenyl)-N-methylisobutyramide [also referred to as "N,N-Me, Isobutyl-CA" (CA=carboxamide)]. Each of the haloanilide compositions of this invention have undergone in vitro toxicity testing on Jurkat cells—this is a T cell line that is sensitivity to toxic effects and thus, was used to determine the effect of the compounds on viability. Each of the compositions of Formula I are capable of inhibiting CRAC channel activity as measured by intracellular calcium influx. It was found that N-methyl-DCPA is effective at lower concentrations. FIGS. 4 and 5 show chemical structures of preferred haloanilide compositions of this invention.

Another embodiment of this invention provides a method of inhibiting osteoclast development comprising administering an effective amount of a haloanilide composition of this invention or a salt thereof, to an osteoclast cell for inhibiting osteoclast development, wherein the haloanilide composition is not N-(3,4-dichlorophenyl)propanamide ("DCPA"). A preferred embodiment of this invention provides wherein the haloanilide composition of this invention is a composition of Formula I, or salt thereof, comprising

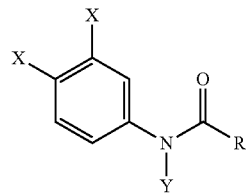

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except wherein X is not chlorine when Y is hydrogen and R is an ethyl group. More preferably, this method as described herein includes wherein the alkyl group has from three to five carbon atoms and the carbon atoms are in either a straight chain or a branch chain arrangement. This method of this invention, as described herein, preferably includes wherein R is an ethyl group, or wherein R is an isopropyl group. Most preferably, this method includes wherein Formula I is a composition selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

Another embodiment of the present invention provides a method for preventing bone erosion in a patient diagnosed with arthritis comprising administering to a patient an effective amount of a haloanilide composition of this invention, or a salt thereof, for preventing bone erosion in a patient, wherein the haloanilide composition is not N-(3,4-dichlorophenyl)propanamide. Preferably, this method of preventing bone erosion, of this invention, includes wherein the haloanilide is a composition of Formula I, or salt thereof, comprising

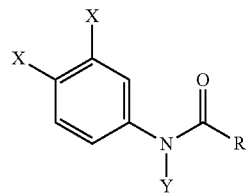

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, wherein X is not chlorine then Y is hydrogen and R is an ethyl group, except wherein X is not chlorine when Y is hydrogen and R is an ethyl group. More preferably, this method, as described herein, includes wherein the alkyl group has from three to five carbon atoms and the carbon atoms are in either a straight chain or a branch chain arrangement. Preferably, this method of this invention includes wherein the R is an ethyl group or an isopropyl group. Most preferably, this method, as described herein, includes wherein Formula I is a composition selected from the group consisting of N-(3,4-dibromophenyl)propanamide, N-(3,4-dichlorophenyl)-N-methylpropanamide, N-(3,4-dichlorophenyl)-N,2- dimethylpropanamide), N-(3,4-dichlorophenyl)-2-dimethylpropanamide, N-(3,4-dichlorophenyl)isobutyramide [also referred to as "DNI"], and N-(3,4-dichlorophenyl)-N-methylisobutyramide.

Another embodiment of this invention provides a method of inhibiting a $Ca^{2+}$ release activated $Ca^{2+}$ (CRAC) channel either in vivo or in vitro comprising subjecting a cell derived from a blood monocyte to an effective amount of a haloanilide composition of this invention, or salt thereof, for inhibiting a $Ca^{2+}$ release activated $Ca^{2+}$ (CRAC) channel of the cell, wherein the haloanilide composition is not N-(3,4-dichlorophenyl)propanamide. In a preferred embodiment of this method, as described herein, the haloanilide is a composition of Formula I, or salt thereof, comprising

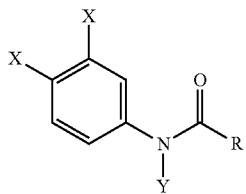

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except wherein X is not chlorine when Y is hydrogen and R is an ethyl group. More preferably, the method includes wherein the alkyl group has from three to five carbon atoms and the carbon atoms are in either a straight chain or a branch chain arrangement. This method, as described herein, preferably includes wherein R is an ethyl group or an isopropyl group. Most preferably, this method, as described herein includes wherein the haloanilide is composition selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], N-(3,4-dichlorophenyl)-N-methylisobutyramide.

Yet another embodiment of this invention provides a composition comprising a haloanilide, or salt thereof, that is a selective inhibitor of a $Ca^{2+}$ release activated $Ca^{2+}$ (CRAC) channel, wherein the haloanilide composition is not N-(3,4-dichlorophenyl)propanamide. Preferably, the compositions of this invention comprise Formula I, or salt thereof,

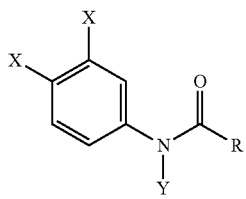

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, except that wherein X is not chlorine when Y is hydrogen and R is an ethyl group. More preferably, the compositions of this invention include wherein the alkyl group has from three to five carbon atoms and the carbon atoms are in either a straight chain or a branch chain arrangement. The compositions of Formula I preferably include wherein R is an ethyl group or wherein R is an isopropyl group. Most preferably, the compositions of this invention are selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide [also referred to as "DNI"], N-(3,4-dichlorophenyl)-N-methylisobutyramide.

Osteoclasts are specialized macrophage derivatives that secrete acid and proteinases to mobilize bone for mineral homeostasis, growth, and replacement or repair. Osteoclast differentiation generally requires the monocyte growth factor m-CSF and the TNF-family cytokine RANKL, although differentiation is regulated by many other cytokines and by intracellular signals, including $Ca^{2+}$. Studies of osteoclast differentiation in vitro were performed using human monocytic precursors stimulated with m-CSF and RANKL, revealing significant loss in both the expression and function of the required components of store-operated $Ca^{2+}$ entry over the course of osteoclast differentiation. However, inhibition of CRAC using either the pharmacological agent 3,4-dichloropropioanilide (DCPA) or by knockdown of Orai I severely inhibited formation of multinucleated osteoclasts. In contrast, no effect of CRAC channel inhibition was observed on expression of the osteoclast protein tartrate resistant acid phosphatase (TRAP). Findings suggest that despite the fact that they are down-regulated during osteoclast differentiation, CRAC channels are required for cell fusion, a late event in osteoclast differentiation. Since osteoclasts cannot function properly without multinucleation, selective CRAC inhibitors may have utility in management of hyperresorptive states (see, Zhou et al., J. Cell. Physiol., Vol. 226, pages 1082-1089, 2011). It is known that osteoclast differentiation from monocytes and regulation of attachment to bone are dependent on inositol 1,4,5-trisphosphate ($InsP_3$)-mediated $Ca^{2+}$-release from the endoplasmic reticulum (ER). Less clear is the extent to which extracellular $Ca^{2+}$ influx is involved osteoclast differentiation. In hematopoietic cells, it is known that $Ca^{2+}$-release-activated $Ca^{2+}$ (CRAC) channel activity represents the major means of $Ca^+$ entry. Further, the type IA transmembrane protein STIMI and the plasma membrane $Ca^{2+}$ channel Orai I have been defined as the molecular mediators of CRAC channel activity.

In CRAC channel activation, the ER luminal portion of the activating protein STIM I, which contains a low-affinity $Ca^{2+}$-binding EF hand mediates activation of Orai I at the cell membrane. In this process, ER $Ca^{2+}$ release, via $InsP_3$ receptors typically, causes a STIM I conformational change that causes STIM I aggregation at sites adjacent to the plasma membrane commonly referred to as puncta. At puncta the cytoplasmic membrane portion of STIM I physically interacts with the plasma membrane-localized $Ca^{2+}$ channel Orai I resulting in its activation. The extent to which this pathway is active during osteoclast differentiation is not established.

The present inventor has studied Orai I and STIM I expression and function during osteoclast differentiation in vitro, and has found significant decreases early in the process of osteoclast differentiation. Further, reduction of Orai I expression with siRNA inhibited osteoclast differentiation, particularly multinucleation. Intriguingly, the addition of the pharmacological agent 3,4-dichloropropioanilide (DCPA) similarly inhibited terminal osteoclast differentiation. DCPA-mediated CRAC channel inhibition occurs via inhibition of STIMI-Orai I interaction. DCPA is a haloanilide compound with relatively low systemic toxicity that can inhibit $Ca^+$ influx in macrophages and T cells as well as having potent anti-inflammatory activity.

In another embodiment of this invention, a method of reducing inflammation in a patient is provided comprising administering to a patient an effective amount of a haloanilide composition or salt thereof, for reducing inflammation in a patient, wherein the haloanilide composition is not N-(3,4-dichlorophenyl)propanamide. Preferably, this method of reducing inflammation in a patient includes wherein the haloanilide is a composition of Formula I, or salt thereof, comprising

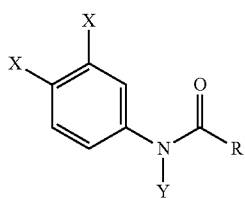

Formula I wherein X is either chlorine or bromine, Y is either hydrogen or an alkyl group having a carbon chain length from 1 to 5 carbon atoms, and R is an alkyl group having a carbon chain length from 1 to 5 carbon atoms, wherein X is not chlorine then Y is hydrogen and R is an ethyl group, except wherein X is not chlorine when Y is hydrogen and R is an ethyl group. More preferably, this method of reducing inflammation in a patient includes wherein the alkyl group has from three to five carbon atoms and the carbon atoms are in either a straight chain or a branch chain arrangement. More preferably, this method of reducing inflammation in a patient includes wherein the R is either an ethyl group or an isopropyl group. Most preferably, this method of reducing inflammation comprises administering to a patient an effective amount of the composition of Formula I that is selected from the group consisting of N-(3,4-dibromophenyl)propanamide, N-(3,4-dichlorophenyl)-N-methylpropanamide, N-(3,4-dichlorophenyl)-N,2-dimethylpropanamide), N-(3,4-dichlorophenyl)-2-dimethylpropanamide, N-(3,4-dichlorophenyl)isobutyramide, and N-(3,4-dichlorophenyl)-N-methylisobutyramide, for reducing inflammation in the patient.

Materials and Methods
Cell Culture, Cell Fines, and Cell Differentiation In Vitro Human monocytes were isolated from normal buffy coat cells (60-80 ml) obtained with approval of institutional review boards by separation from donor blood, the white-cell depleted blood retained for clinical use. Human monocyte culture and differentiation were as reported (see, Yaroslayskly B B, Zhang Y, Kalla S E, Garcia P V, Sharrow A C, Li Y, Zaidi M, Wu C, Blair H C, "NO-dependent osteoclast motility: Reliance on cGMP-dependent protein kinase I and VASP", J Cell Sci I, Vol. 18, pages 5479-5487, 2005). Briefly, human monocytes cells were isolated from buffy coat on ficoll lymphocyte separation media and cultured at ~$6\times10^5$ cells per $cm^2$ in monocyte maintenance medium, Dulbecco's modified essential medium (DMEM) with 20 ng/ml of human m-CSF and 10% FBS, for 24 hours (h). After 24 h in culture, the medium was changed to osteoclast differentiation medium containing in addition of human 50 ng/ml of RANKL, with the additional inhibitors or activators as specified in results. Human osteoclast cultures were generally maintained for a minimum of 7 days before analysis, or longer times as specified in results. Characterization of osteoclasts included in situ demonstration of tartrate resistant acid phosphatase (TRAP) using naphthol phosphate substrate coupled with fast garnet at pH 5 in 200 mM tartrate (leucocyte acid phosphatase, Sigma-Aldrich, St. Louis, Mo.) and by evaluation of multinucleation using either phase contrast microscopy or nuclear stains.

Western Blots

Cells were lysed in 1% NP-40 (nonyl phenoxylpoly-ethoxylethanol), 150 mM NaCl, 50 mM Tris, pH 8.0, with proteinase inhibitors, cleared by centrifugation, and normalized for protein, determined by Bradford dye-binding. Proteins were resolved by electrophoresis on 8% polyacrylamide in sulfonyl dodecyl sulfate, and transferred to polyvinylidene difluoride derivitized nylon. Membranes were blocked in Tris-buffered saline with 0.05% polyoxyethylene sorbitan (Tween 20) with 5% bovine serum albumin, 1 h, 20° C. (centigrade), and incubated with the primary antibodies at 4° C. overnight. Membranes were washed and the appropriate peroxidase-conjugated secondary antibody added. After a 30-min (minute) incubation, membranes were washed and bands were visualized by enhanced chemiluminescence (ECL-Western Blot Reagent Kit, GE Healthcare, Waukesha, Wis.).

Electro Physiology

Analysis was performed in HEK293 cells stably expressing Orai I and transfected with STIM I YFP used conventional whole cell voltage recordings as described (see, Wang Y, Deng X, Zhou Y, Hendron E, Mancarelia S, Ritchie M F. Tang X D, Baba Y, Kurosaki T, Mori Y, Soboloff J, Gill D L., "STIM protein coupling in the activation of Orai channels", Proc Natl Acad Sci USA Vol. 106, pages 7391-7396, 2009). Immediately after establishment of the whole-cell electrode seal, voltage ramps spanning from—100 to +100 mV in 50 msec were delivered from a holding potential of 0 mV at a rate of 0.5 Hz. A 10 mV junction potential compensation was applied. The intracellular solution contained 145 mM CsGlu, 10 mM HEPES, 10 mM EGTA, 8 mM NaCl, 6 mM $MgCl_2$, and 2 mM Mg-ATP (total 8 mM $Mg^{2+}$), pH 7.2; TRPM7 activity was suppressed by 8 mM $Mg^{2+}$ and ATP (see, Zhou Y, Mancarella S, Wang Y, Yue C, Ritchie M, Gill D L, Soboloff J, "The short N-terminal domains of STIM I and STIM2 control the activation kinetics of Orai I channels", J Biol Chem, Vol. 284, pages 19164-19168, 2009). The extracellular solution contained 145 mM NaCl, 10 mM $CaCl_2$, 10 mM CsCl, 2 mM $MgCl_2$, 2.8 mM KCl, 10 mM HEPES, and 10 mM glucose, pH 7.4.

DNA and RNA Reagents
PCR Primers:

Homo sapiens $Ca^{2+}$ release-activated $Ca^{2+}$ modulator I (ORAI I) NM_032790, commercially available from OriGene, Rockville, Md.

Homo sapiens glyceraldehyde-3-phosphate dehydrogenase (GAPDH) NM_002046, commercially available form OriGene, Rockville, Md.

Orai I silencing used a pool of four siRNAs targeting Homo sapiens ORAI I (GenBank NM_032790), purchased as a pretested reagent from Dharmacon RNAi Technologies (smartpool 84876, Thermo-Fisher, Waltham, Mass.). Cells were transfected using siPORTAmine (Ambion, Austin, Tex.), a blend of polyamines, as described (see, Yaroslayskly et al., 2005, above). Controls were transfected with nonsense siRNA.

To visualize transfection, Cy5 was covalently attached to the duplex siRNA (Ambion Silencer siRNA labeling kit). mRNA was quantified by real-time PCR as described in Robinson L j, Yaroslayskly B B, Griswold R D, Zadorozny E V, Guo L, Tonrkova I L, Blair H C, "Estrogen inhibits RANKL-stimulated osteoclastic differentiation of human monocytes through estrogen and RANKL-regulated interaction of estrogen receptor-alpha with BCARI and Traf6", Exp Cell Res, Vol. 315, pages 1287-1301, 2009.

STIM I Puncta Formation

HEK293 cells, maintained in DMEM with 10% FBS, were transfected with YFP-STIM I using Lipofectamine 2000 (Invitrogen, Carlsbad, Calif.) for 5 h (37° C.; 5% $CO_2$) followed by a 24-h recovery. Cells were placed in 140 mM NaCl, 5 mM KCl, 1 mM $MgCl_2$, 10 mM glucose, 15 mM HEPES, 0.1% BSA, 2 mM $CaCl_2$ and analyzed by confocal microscopy for STIM I puncta formation using a Nikon phase-fluorescence microscope with CCD detectors (Diagnostic instruments, Sterling Heights, Mich.). Phase or transmitted light microscopy used 10-40× objectives and red, green, and blue filters to assemble color images. Fluorescence images used 1.4 NA 40× oil objectives. Red fluorescence used excitation at 530-560 nm, a 575 nm dichroic minor, and 580-650 nm emission filter. Transfection data were analyzed using Nikon NIS Elements Imaging Software. The effect of DCPA on STIM I/Orai I association was determined in wild-type HEK293 cells transfected with STIM I-YFP as described in Wang Y, Deng X, Zhou Y, Hendron E, Mancarelia S, Ritchie M F, Tang X D, Baba Y, Kurosaki T, Mori Y, Soboloff J, Gill DL, "STIM protein coupling in the activation of Orai channels", Proc Natl Acad Sci USA, Vol. 106, pages 7391-7396, 2009. Experiments were performed on a Leica DMI 6000B fluorescence microscope controlled by Slidebook Software (Intelligent Imaging Innovations, Denver, Colo.).

Cytosolic $Ca^{2+}$ Measurement

Ratiometric imaging of intracellular $Ca^{2+}$ using fura-2 was as described (see, Zhou et al., 2009 above). Briefly, cells on coverslips, in cation safe solution (107 mM NaCl, 7.2 mM KCl, 1.2 mM $MgCl_2$, 11.5 mM glucose, 20 mM HEPES-NaOH, pH 7.2) were loaded with fura-2 acetoxymethyl ester (2 µM) for 30 min at 24° C. Cells were washed and fluorescent probe was allowed to de-esterify for 30 min. From signal remaining after saponin permeabilization, ~85% of the dye was confined to the cytoplasm (see, Ma H-T, Patterson R L. van Rossum D B. Birnbaumer L, Mikoshiba K, Gill D L, "Requirement of the inositol trisphosphate receptor for activation of store-operated $Ca^{2+}$ channels", Science, Vol. 287, pages 1647-1651, 2000). $Ca^{2+}$ measurements were made using a Leica DMI 6000B fluorescence microscope controlled by Slidebook Software. Fluorescence emission at 505 nm was monitored while alternating between 340 and 380 nm excitation wavelengths at a frequency of 0.67 Hz; intracellular $Ca^{2+}$ measurements are shown as 340/380 nm emission ratios obtained from groups (35-45) of single cells. Measurements shown are representative a minimum of three independent experiments.

Materials

The inhibitor DCPA was from ChemServices (West Chester, Pa.). Working solutions were made in ethanol at 1,000× final concentration, with equal ethanol added to controls. The inactive congener 3,4-difluoropropioanilide was synthesized by fluorination of propionanilide methyl ester; the product was de-esterified and purified by column chromatography, with identification of the purified product by spectroscopy.

Results $Ca^{2+}$ Homeostasis During Osteoclast Differentiation

Store-dependent and store-independent changes in cytosolic $Ca^{2+}$ concentration were examined in human monocytes isolated from buffy coat as they differentiated into osteoclasts in vitro (FIG. 1A-1G). Cultures maintained in m-CSF were treated with RANKL to induce and support osteoclast differentiation for 1, 3, 7, or 11 days. At each of these time points, cultures were loaded with Fura 2 to measure basal cytosolic $Ca^{2+}$ concentration (FIG. 1A-1G) and samples were collected for Western analysis (FIG. 1H). Intriguingly, irrespective of the presence of extracellular $Ca^{2+}$, spontaneous $Ca^{2+}$ fluxes were observed in a significant percentage of these cells (FIG. 1A-1E). Further, the percentage of cells exhibiting these spontaneous $Ca^{2+}$ fluxes increased the longer cells were maintained in RANKL, reaching as high as 75% at day 11 (FIG. 1F). To assess the capacity of these cells for store-operated $Ca^{2+}$ entry, they were then treated with the Sarco/Endoplasmic Reticulum (SERCA) inhibitor thapsigargin in the absence of extracellular $Ca^{2+}$ to deplete ER $Ca^{2+}$ content. The subsequent addition of 1 mM $Ca^{2+}$ revealed significant decreases in the amount of $Ca^{2+}$ entry between 1 and 11 days after the addition of RANKL (FIG. 1A-1E, and FIG. 1G). Interestingly, this decrease in the capacity for store-operated $Ca^{2+}$ entry during osteoclast differentiation coincided with decreases in the expression of STIMI, STIM2 and Orai I (FIG. 1H). Hence, not only does RANKL induce $Ca^{2+}$ oscillations, but also this invention reveals dramatic changes in both the expression and function of proteins involved in store-operated $Ca^{2+}$ entry during RANKL-induced osteoclast differentiation.

Reduced Expression of Orai I Reduces Multinucleation of Human Osteoclasts In Vitro To assess the contributions of CRAC channels towards osteoclast differentiation, human monocytes were treated with CyS-labeled Oraii siRNA and differentiated in vitro into osteoclasts. Transfection efficiency with an siRNA cocktail was ~75% (FIG. 2A), with the ~80% decrease in Orai I protein by Western analysis (FIG. 2B) suggesting that very little Orai I was present in cells that were transfected. Orai I mRNA was also measured in cells at the time of plating and after RANKL addition for 3, 7, and 11 days (FIG. 2C). Orai I mRNA relative to GAPDH was reduced 60% at day 3, but message levels increased overtime, in keeping with loss of siRNA. Irrespective, transfection with Orai I siRNA resulted in a 58% decrease in SOCe relative to control 11 days after RANKL addition. Interestingly, addition of RANKL had no effect on Orai I at the RNA level (FIG. 2D), distinct from what was observed for Orai I protein expression (FIG. 1H). Nevertheless, knockdown of Orai I markedly reduced the number of multinucleated cells after 7 days (FIG. 2E, histogram and arrows in middle photomicrograph); multinucleated syncytia are required for efficient bone degradation and reduced multinucleated cells are a characteristic of osteopetrosis. However, other properties of osteoclasts include induction of TRAP and TRAP activity was similar in control and Orai knockdown cultures (FIG. 2E, arrowheads in photomicrograph), suggesting that the reduction in multinucleation is distal to induction of key osteoclast proteins.

Pharmacological Inhibition of Store-Operated Calcium Entry (SOCe) Reduces Multinucleation of Human Osteoclasts The haloanilide DCPA blocks store-operated $Ca^{2+}$ channel function in Jurkat cells with no effect on ER $Ca^{2+}$ content. DCPA also reduced SOCe in osteoclasts by 27.5% (n=3; data not shown). Whether effects of DCPA result from direct modulation of store-operated $Ca^{2+}$ channels was not known. To address this, the present inventor examined HEK293 cells stably expressing Orai I and transiently transfected with YFP-STIMI and measured the effect of DCPA on CRAC current or $I_{crac}$. CRAC channel activity was measured in the whole cell clamp position after passively depleting $Ca^{2+}$ stores via the presence of 10 mM EGTA in the patch pipette. In both control and DCPA-treated cells, CRAC current began to develop within 30 sec of break-in. However, CRAC currents began to close prior to reaching the peak in DCPA-treated cells, returning to baseline less than 4 minutes after break-in. Analysis of the current-voltage relationship between control and DCPA-treated cells did not show significant differences. These observations demonstrate that DCPA is a bona-fide CRAC channel inhibitor, although its mechanism of action was not yet defined.

Figure 2:
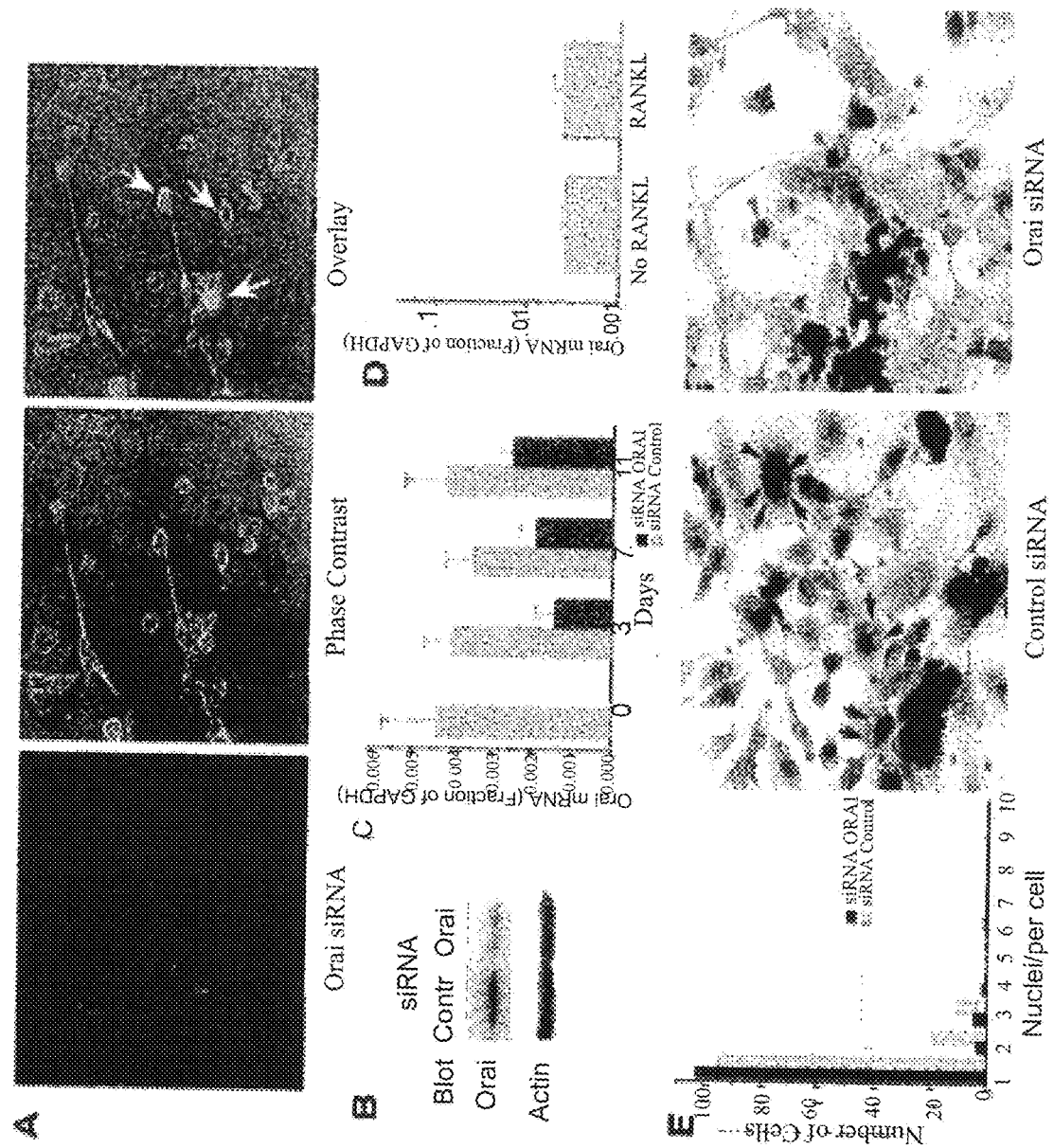
FIGS. 2A-2E show siRNA knockdown of Orai inhibits human osteoclast developments in vitro.

The effect of DCPA on human osteoclast differentiation 8 days after addition of RANKL was evaluated. Osteoclast differentiation is demonstrated by multinucleated (>2 nuclei/cell) cells and TRAP activity. DCPA was added at 1.0, 10, and 100 µM to identical cultures at the time of RANKL addition; 1.0 µM DCPA had minimal effect on the number of multinucleated TRAP$^+$ cells, but there was a marked progressive reduction in the number of multinucleated cells at 10 and 100 µM DCPA. Despite qualitative differences in cell clumping and other secondary features of the cultures, no differences in the TRAP activity were observed even at the highest concentration of inhibitor, in keeping with results of Orai knockdown (FIG. 2). The inactive DCPA congener 3,4-difluororopropioanilide [also referred to as "DFPA" or "3,4-difluoropropanamide") had no significant effect on multinucleation at either 10 µM or 100 µM, indicating that DCPA-mediated inhibition of osteoclast formation results from CRAC inhibition.

DCPA Reduces Puncta Formation by CRAC Channel Components in Wild-Type HEK293 Cells or HEK293 Cells Overexpressing STIMI and Orai I Based on the investigation above, it was found that DCPA inhibits CRAC-mediated $Ca^{2+}$ influx. A series of experiments to test the possibility that DCPA inhibits STIM 1-Orai I interaction were performed. When ER $Ca^{2+}$ stores are depleted, $Ca^{2+}$ is released from the STIM I EF-hand leading to its aggregation near the plasma membrane in structures often referred to as puncta. Therefore, HEK293 cells transiently transfected with YFP-STIM I were examined to determine the effect of DCPA on STIM I puncta formation using fluorescence microscopy. Prior to treatment, all cells displayed a diffuse distribution of YFP-STIM I. However, depletion of ER $Ca^{2+}$ stores with 2 µM thapsigargin led consistently to extensive puncta formation in control cells within 7.5 minutes. In contrast, DCPA treatment dramatically inhibited puncta formation after depleting $Ca^{2+}$ stores over a 16 minute period. Hence, a relatively small number of puncta appeared in specific location, but the overall distribution of YFP-STIM I in DCPA-pretreated cells was considerably more diffuse than control cells. Considered in combination with our CRAC measurements, these findings are consistent with an effect of DCPA on STIM I aggregation and/or interaction with Orai I.

Further, in cells overexpressing both Orai I and the cytosolic fragment of STIM I (STIM 1 ct), a second CRAC channel modulator, 2-aminoethoxydiphenylborate (2-APB), causes STIM 1 ct to translocate to the plasma membrane and interact with Orai I. To determine if DCPA modulates interactions between STIM I and Orai I, a similar experiment was done in the presence or absence of DCPA. YFP-STIM I ct was evenly distributed throughout the cytoplasm prior to the addition of 2-APB (50 µM). As early as 5 seconds after the addition of 2-APB, significant translocation of STIM I ct towards the PM could be seen. STIM I ct remains localized to the plasma membrane for at least several minutes after addition of 2-APB. However, when this experiment was repeated in the presence of DCPA (100 µM), the ability of 2-APB to induce STIM I ct translocation to the plasma membrane was dramatically attenuated. As such, our data indicate that DCPA inhibits STIM I/Orai I interaction, likely by inhibiting STIM I aggregate formation.

Thus, this invention demonstrates marked changes in $Ca^{2+}$ homeostasis during RANKL-mediated osteoclast differentiation. Interestingly, coincident with an increase in spontaneous $Ca^{2+}$ oscillations, it was observed that a decreased functional activity and expression of the CRAC channel components, Orai I, STIM I, and STIM2. However, this did not reflect a reduced role for Orai I in differentiating osteoclasts; either reducing Orai I expression with small interfering RNA or interfering with its function using DCPA markedly inhibited osteoclast differentiation. Indeed, osteoclast differentiation, particularly multinucleation, occurred at very low rates when Orai expression and/or activity were suppressed.

The addition of RANKL caused complex changes in $Ca^{2+}$ homeostasis; apparently spontaneous $Ca^{2+}$ oscillations were observed throughout the differentiation period, events which coincided with significant changes in the expression and function of the SOCe components STIMI and Orai I (FIG. 1). The role for SOCe in multinucleation is disclosed in this invention, however RANKL-induced $Ca^{2+}$ oscillations in differentiating osteoclasts is known. $Ca^{2+}$ oscillations were attributed to InsP3R activity downstream of RANK-dependent ROS production. $Ca^{2+}$ fluxes could be observed in cells for as long as 30 minutes after removal of extracellular $Ca^{2+}$ (data not shown). These observations show that osteoclast differentiation is highly $Ca^+$-dependent, requiring expression of the InsP3R to mediate the activation of NFATc1, the critical player in osteoclastogenesis. The present invention discloses that SOCe is specifically required for terminal differentiation, yet dispensable for earlier events in osteoclast differentiation.

In prior studies where NFATc1 expression was silenced or overexpressed, changes in osteoclast generation correlated directly with similar changes in the number of TRAP$^+$ cells. In the studies reported herein, blockage of $Ca^{2+}$ influx inhibited multinucleation but did not inhibit TRAP activity. A potential explanation for this difference would be that the spontaneous and extracellular $Ca^{2+}$-independent $Ca^{2+}$ fluxes that were observed throughout the osteoclast differentiation period are sufficient to activate NFATc1 and induce TRAP expression, but insufficient to induce cell fusion. It is interesting to note that the plasma membrane $Ca^{2+}$ channel TRPV4 has also been shown to be important for terminal differentiation in osteoclasts. However, trpv4$^{-/-}$ mice differ significantly in phenotype from Orai I$^{-/-}$ in that trpv4$^{-/-}$ show increased bone mass attributed to reduced bone resorption, whereas Orai I$^{-/-}$ show poor bone development. Irrespective, considered collectively, it seems clear that whereas early events in osteoclastogenesis depend on InsP3R and ROS, osteoclast fusion is highly dependent on extracellular $Ca^+$.

Previously, it has been established that DCPA can inhibit store-operated $Ca^{2+}$ entry, although the mechanisms whereby this was achieved were entirely unclear. In addition to demonstrating its potential as an inhibitor of osteoclastogenesis, it has now been shown that the channels inhibited by DCPA are specifically CRAC channels. This invention shows that this inhibition results from interference of STIM-Orai interaction.

Figure 3:
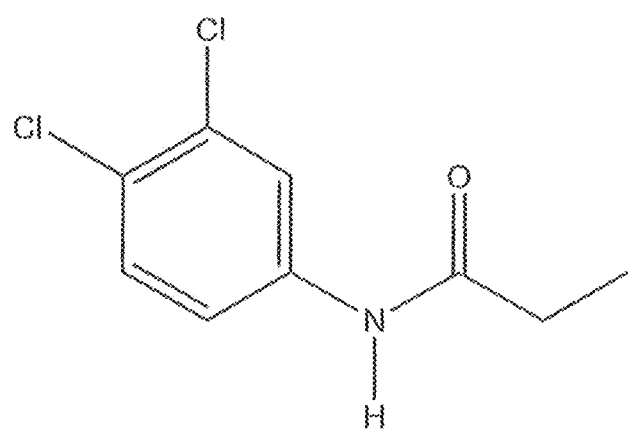
FIG. 3 shows the known chemical structure of N-(3,4-dichlorophenyl)propionamide, also known as "DCPA" or "N-(3,4-dichlorophenyl)propanamide" or "PROPANIL".

FIG. 3 shows the known chemical structure of N-(3,4-dichlorophenyl)propionamide, also known as "DCPA" or "N-(3,4-dichlorophenyl)propanamide" or "PROPANIL".

FIG. 4 shows the chemical structures of the more preferred haloanilide compositions of the present invention, namely, N-(3,4-dibromophenyl)propionamide (also known as "DBPA" or "N-(3,4-dibromophenyl)propanamide"), and N-(3,4-dichlorophenyl)-N-methylpropionamide (also known as "N,N-Me,Propyl-CA" or "N-Methyl-DCPA" or "NMP" or N-(3,4-dichlorophenyl)-N-methylpropanamide".

FIG. 5 shows the chemical structures of the more preferred haloanilide compositions of the present invention, namely, N-(3,4-dichlorophenyl)isobutylamide (also known as "N-Isobutyl-CA" or "DNI"), and N-(3,4-dichlorophenyl)-N-methylisobutyramide (also known as "N,N-Me,Isobutyl-CA").

Figure 6:
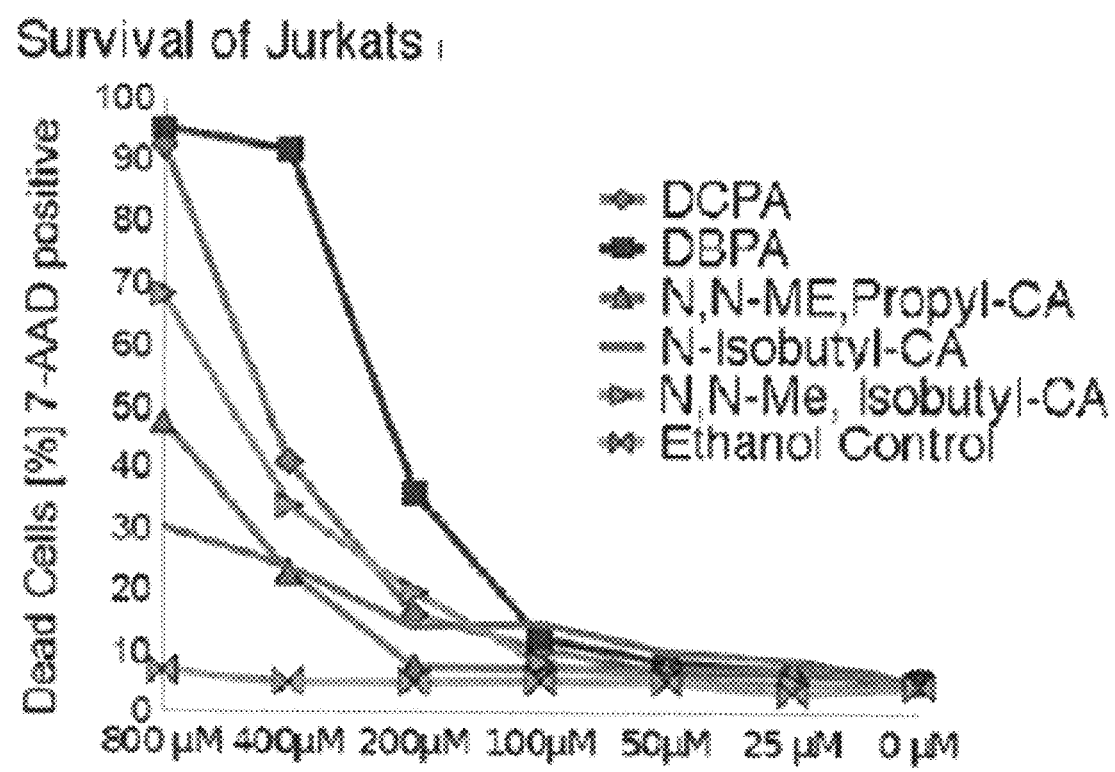
FIG. 6 shows a graph having the toxicity results of DCPA; DBPA; N,N-Me,Propyl-CA; N-Isobutyl-CA; N,N-Me, Isobutyl-CA; and ethanol control on Jurkat cells exposed 48 hours to each of these compositions, respectively, at the concentrations indicated on the x-axis of the graph, and analyzed by flow cytometry using the far-red fluorescent DNA binding probe 7-aminoactinomycin D (i.e. 7-AAD) to indicate dead or late apoptotic cells indicated on the y-axis of the graph.

FIG. 6 shows a graph having the toxicity results of DCPA; DBPA; N,N-Me,Propyl-CA; N-Isobutyl-CA; N,N-Me, Isobutyl-CA; and ethanol control on Jurkat cells exposed 48 hours to each of these compositions, respectively, at the concentrations indicated on the x-axis of the graph, and analyzed by flow cytometry using the far-red fluorescent DNA binding probe 7-aminoactinomycin D to indicate dead or late apoptotic cells.

Figure 7:
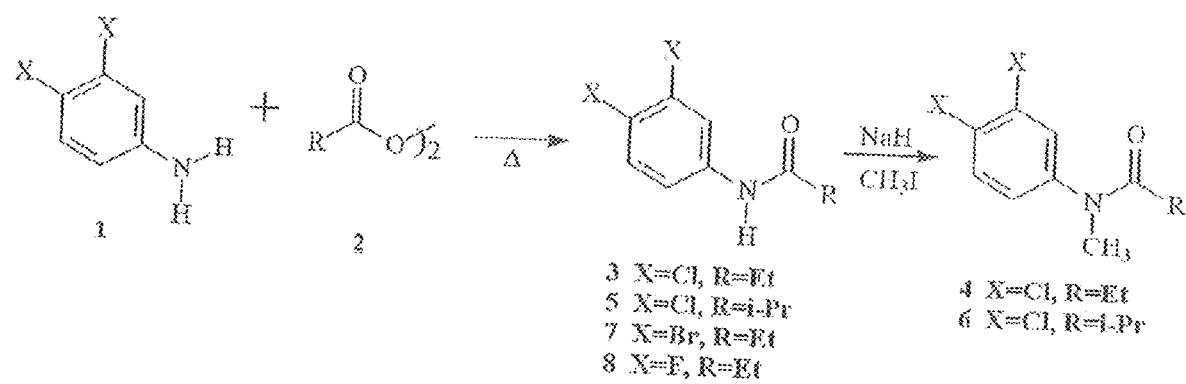
FIG. 7 shows synthesis scheme for the compositions of the present invention.

FIG. 7 shows synthesis scheme for the compositions of the present invention. In FIG. 7, compositions of the present invention identified by numerals 4-7 are prepared by condensation of compounds 1 and 2, neat with mild heating and methylation (4 and 6, eqn 1). The condensation products were isolated by filtration after quenching with water and purified by recrystallization. Methylation was achieved by forming the sodium salt with NaH, treatment with methyl iodide and recrystallization of the product.

Figure 8:
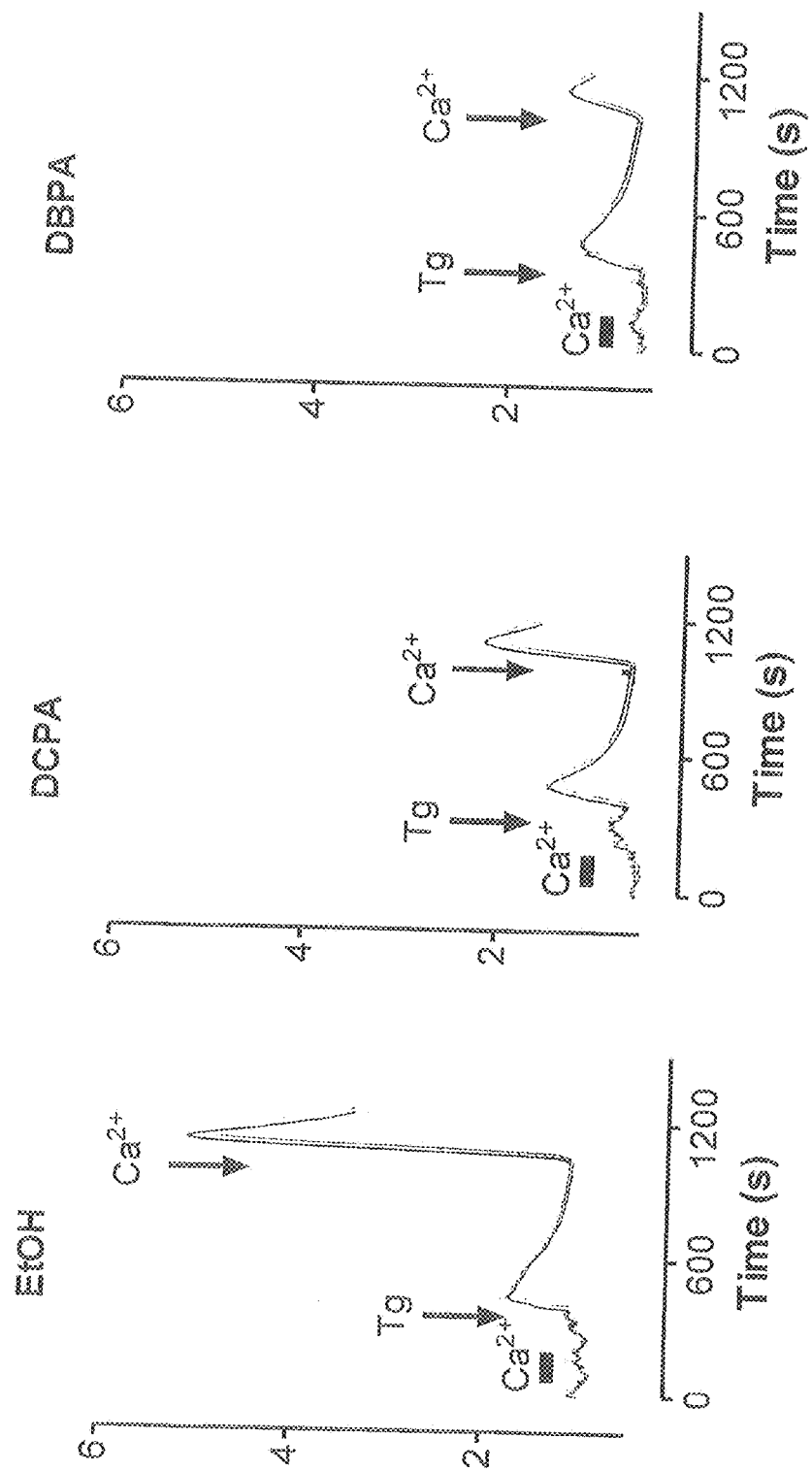
FIG. 8 shows inhibition of CRAC channels with a composition of the present invention, namely, DBPA [ie. N-(3, 4-dibromophenyl)propanamide].

FIG. 8 shows inhibition of CRAC channels with a composition of the present invention, namely, DBPA [ie. N-(3,4-dibromophenyl)propanamide]. Jurkat cells, a T cell line that is very sensitive to DCPA, was cultured with the indicated compounds, DCPA, DBPA, and ethanol (EtOH). CRAC channel activity was monitored using Fura-2 fluorescence using standard known techniques. Cells were incubated in each composition at 100 uM for 10 minutes prior to addition of the SERCA inhibitor thapsigargin (Tg) to induce SOCe. Decreased CRAC channel activity is clearly evident with DCPA and DBPA. However, DBPA of the present invention does not have the burden of toxicity of DCPA that would accompany further metabolism of DCPA.

Figure 9:
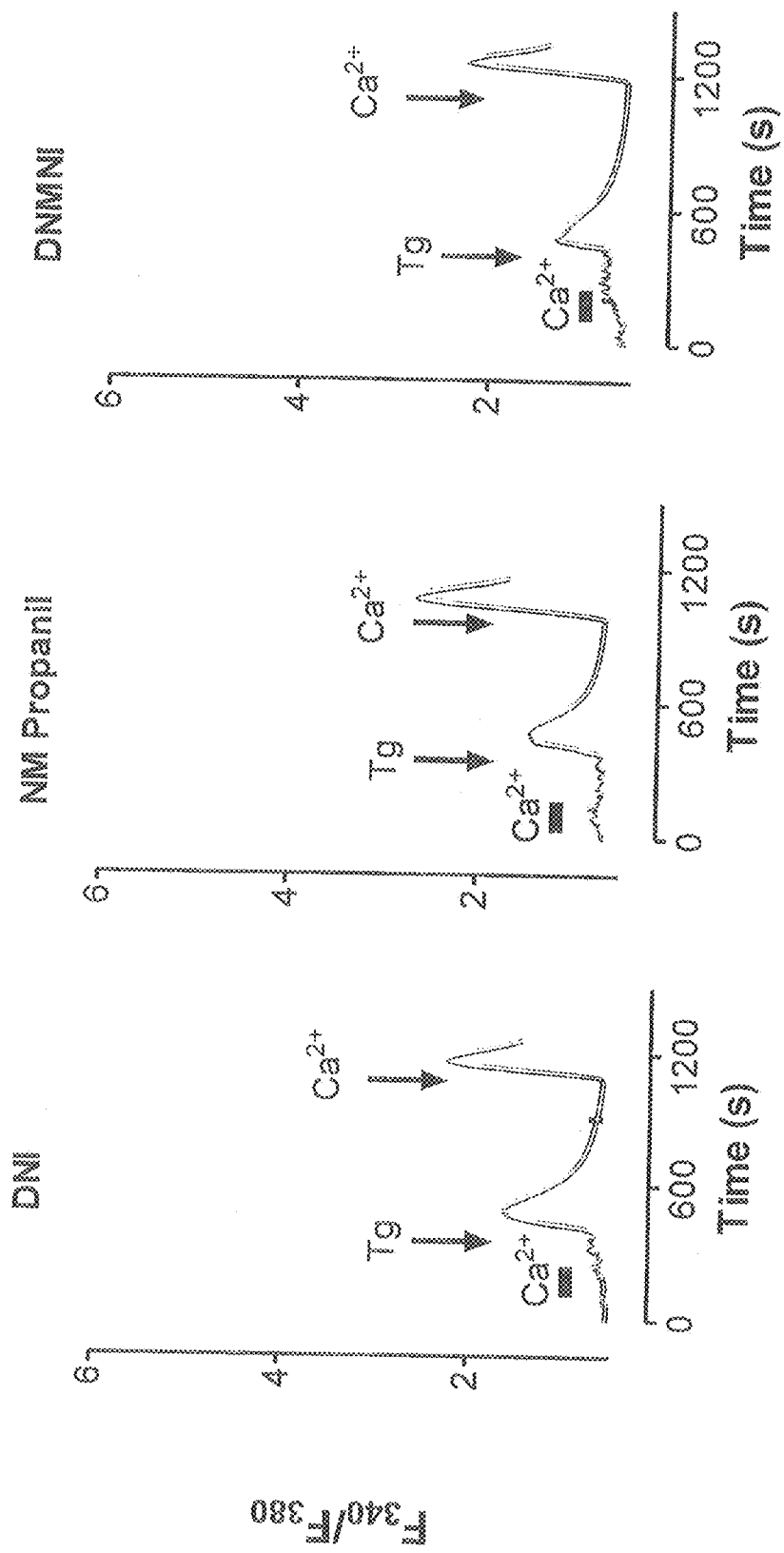
FIG. 9 shows inhibition of CRAC channels with compositions of the present invention, namely, DNI, NM Propanil, and DNMNI.

FIG. 9 shows inhibition of CRAC channels with compositions of the present invention, namely, DNI, NM Propanil, and DNMNI. Jurkat cells, a T cell line that is very sensitive to DCPA, was cultured with the indicated compositions of the present invention, namely, DNI, NM Propanil, and DNMNI. CRAC channel activity was monitored using Fura-2 fluorescence using standard known techniques. Cells were incubated in each composition at 100 uM for 10 minutes prior to addition of the SERCA inhibitor thapsigargin (Tg) to induce SOCe. Decreased CRAC channel activity is clearly evident with each of the compositions of the present invention. Each of the compositions of the present invention showed similar levels of inhibition as the known DCPA. Each of the compositions of this invention achieve the results achieved with the known DCPA but without the burden of toxicity of DCPA that would accompany further metabolism of DCPA.

Figures 10A, 10B:
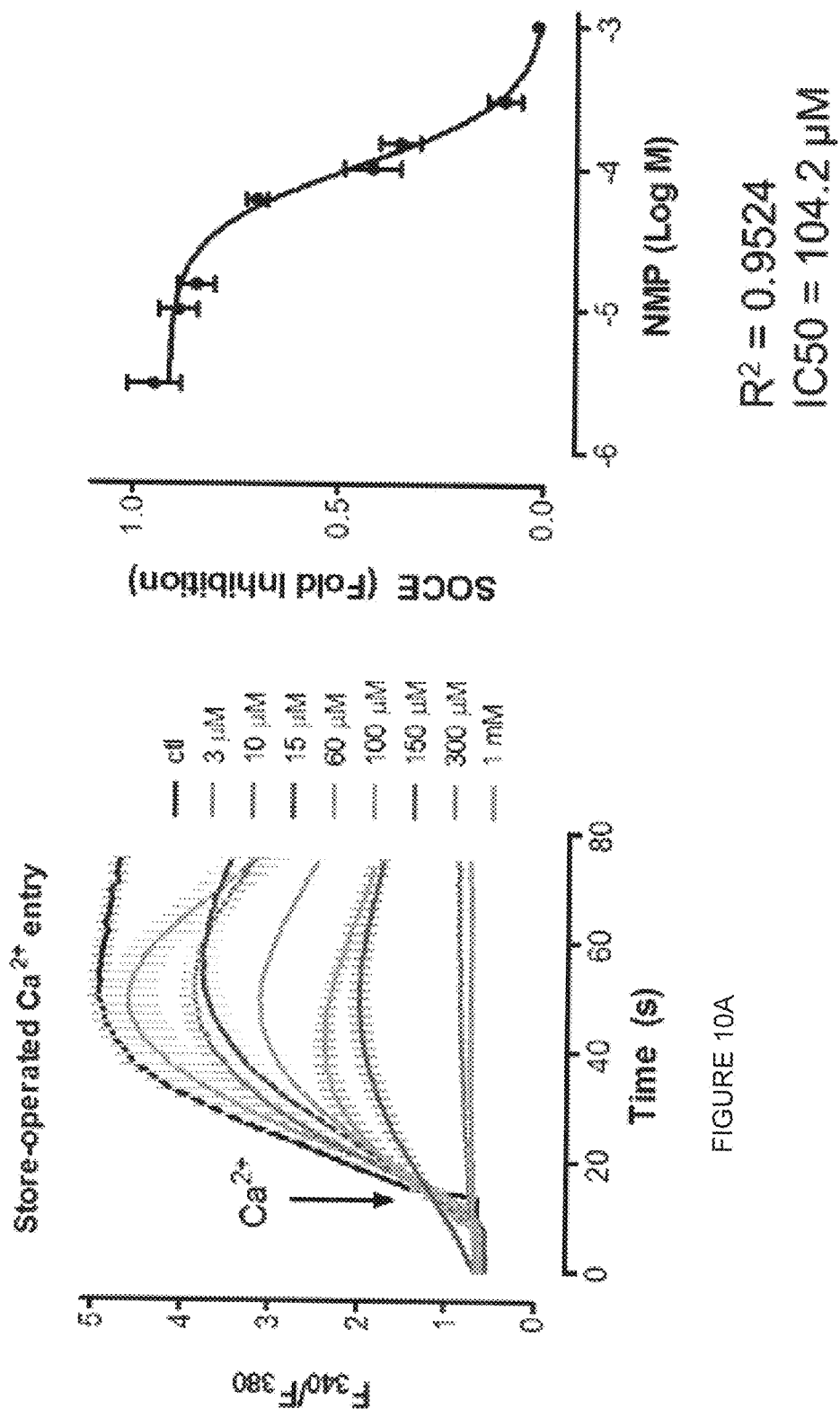
FIG. 10A shows the dose response of a composition of the present invention, namely, N-(3,4-dichlorophenyl)-N-methylpropanamide (also known as "NMP" or "N-methyl DCPA") at doses of 3 µM, 10 µM, 15 µM, 60 µM, 100 µM, 150 µM, 300 µM, and 1 mM, respectively.
FIG. 10B shows Store-Operated Calcium Entry (SOCE) inhibition of NMP having a $IC_{50}$ of 104.2 µM.

FIG. 10A shows the dose response of a composition of the present invention, namely, N-(3,4-dichlorophenyl)-N-methylpropanamide or "NMP" or "N-methyl DCPA" at doses of 3 µM, 10 µM, 15 µM, 60 µM, 100 µM, 150 µM, 300 µM, and 1 mM, respectively, which is at least equal to that of the known DCPA composition. FIG. 10B shows Store-Operated Calcium Entry (SOCE) inhibition of NMP having a $IC_{50}$ of 104.2 µM.

It will be appreciated by those persons skilled in the art that the present invention shows that the CRAC channel is a $Ca^{2+}$ channel required for normal osteoclast differentiation in vitro. Further, based on the demonstrated effect of DCPA on SOCe via inhibition of STIM I puncta, siRNA knockdown of Orai I and the lack of an effect of these treatments on TRAP staining in monocytes after RANKL and m-CSF stimulation, this invention discloses that induction of TRAP activity is not dependent on extracellular $Ca^{2+}$. In contrast, multinucleation, another key characteristic of osteoclast differentiation, is dependent on functional CRAC channels. As such, the haloanilide compositions of the present invention and methods provided $Ca^{2+}$ channel inhibitors that impact the role of osteoclasts in osteoporosis, osteopetrosis, and bone degradation associated with arthritis.

These terms and specifications, including examples, serve to describe the invention by example and not to limit the invention. Whereas particular embodiments of this invention have been described for purposes of illustration, it will be evident to those persons skilled in the art that numerous variations of the details of the present invention may be made without departing from the invention as defined herein and in the appended claims.

What is claimed is:

1. A method of inhibiting osteoclast development comprising:
   administering an effective amount of a haloanilide composition or a salt thereof to an osteoclast cell for inhibiting osteoclast development, wherein said haloanilide composition is not N-(3,4-dichlorophenyl) propanamide, and wherein said haloanilide is a composition of Formula I, or salt thereof, comprising

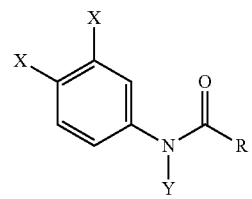

Formula I wherein X is chlorine, wherein R is an ethyl group, and wherein Y is a methyl group.

2. A method for preventing bone erosion in a patient diagnosed with arthritis comprising:
   administering to a patient an effective amount of a haloanilide composition or salt thereof for preventing bone erosion in a patient diagnosed with arthritis, wherein said haloanilide composition is not N-(3,4-dichlorophenyl)propanamide, and wherein said haloanilide is a composition of Formula I, or salt thereof, comprising

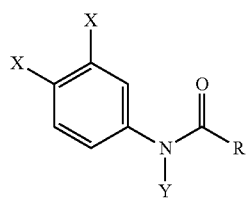
Formula I
wherein X is chlorine, wherein R is an ethyl group and Y is a methyl group.
* * * * *